(12) United States Patent
Barberan et al.

(10) Patent No.: US 9,271,909 B2
(45) Date of Patent: Mar. 1, 2016

(54) CLEANSING COMPOSITION

(75) Inventors: Pilar Castan Barberan, Barcelona (ES); Michael Stapels, Kleve (DE); Takashi Masui, Chiba (JP); Hiroki Takeuchi, Tokyo (JP); Masahiro Miyaki, Tokyo (JP)

(73) Assignees: KAO CORPORATION, Tokyo (JP); KAO CORPORATION, S.A., Barbera del Valles (ES)

( * ) Notice: Subject to any disclaimer, the term of this patent is extended or adjusted under 35 U.S.C. 154(b) by 168 days.

(21) Appl. No.: 13/877,969

(22) PCT Filed: Oct. 5, 2011

(86) PCT No.: PCT/EP2011/067371
§ 371 (c)(1),
(2), (4) Date: May 31, 2013

(87) PCT Pub. No.: WO2012/045768
PCT Pub. Date: Apr. 12, 2012

(65) Prior Publication Data
US 2013/0239985 A1    Sep. 19, 2013

(30) Foreign Application Priority Data

Oct. 5, 2010   (EP) .................................... 10186522

(51) Int. Cl.
*A61K 8/39*   (2006.01)
*A61Q 19/10*   (2006.01)
*A61K 8/46*   (2006.01)

(52) U.S. Cl.
CPC . *A61K 8/39* (2013.01); *A61K 8/463* (2013.01); *A61Q 19/10* (2013.01); *A61K 2800/592* (2013.01)

(58) Field of Classification Search
CPC ... A61K 8/39; A61K 8/463; A61K 2800/592; A61Q 19/10
See application file for complete search history.

(56) References Cited

U.S. PATENT DOCUMENTS

| | | |
|---|---|---|
| 5,607,678 A | 3/1997 | Moore et al. |
| 5,632,978 A | 5/1997 | Moore et al. |
| 5,866,110 A | 2/1999 | Moore et al. |
| 6,444,629 B1 | 9/2002 | Elliott et al. |
| 2002/0128162 A1 | 9/2002 | Elliott et al. |
| 2002/0165103 A1 | 11/2002 | Tsaur et al. |
| 2006/0233733 A1 | 10/2006 | Beauquey et al. |
| 2009/0023623 A1 | 1/2009 | Yamamoto et al. |
| 2014/0228269 A1 | 8/2014 | Masui et al. |

FOREIGN PATENT DOCUMENTS

| | | | |
|---|---|---|---|
| CN | 1190987 A | 8/1998 | |
| CN | 1875917 A | 12/2006 | |
| EP | 0 994 178 | 4/2000 | |
| EP | 1 213 007 | 6/2002 | |
| EP | 2 042 587 | 4/2009 | |
| JP | 6 346259 | 12/1994 | |
| JP | 2008-308492 A | 12/2008 | |
| JP | 2013-53093 A | 3/2013 | |
| WO | 96 05798 | 2/1996 | |
| WO | WO 96/37591 A1 | 11/1996 | |
| WO | 99 09947 | 3/1999 | |
| WO | 99 09949 | 3/1999 | |
| WO | 99 09950 | 3/1999 | |
| WO | 99 09951 | 3/1999 | |
| WO | 02 074252 | 9/2002 | |
| WO | WO2009040370 | * 4/2009 | ........... C10M 173/02 |

OTHER PUBLICATIONS

International Search Report Issued Feb. 21, 2012 in PCT/EP11/67371 Filed Oct. 5, 2011.

* cited by examiner

*Primary Examiner* — Suzanne Ziska
*Assistant Examiner* — Thurman Wheeler
(74) *Attorney, Agent, or Firm* — Oblon, McClelland, Maier & Neustadt, L.L.P

(57) ABSTRACT

A cleansing composition containing the following components (A) and (B): (A) an ether carboxylate of Formula (1) $R^1$—O—$(CH_2CH_2O)_n$—$CH_2$—COOX (1) wherein —$R^1$ represents a linear or branched $C_4$-$C_{10}$ alkyl or alkenyl group, —n represents a number from 0.5 to 20, and —X represents a hydrogen atom or a cation selected from the group consisting of an alkali metal, an alkaline earth metal, ammonium, an alkylammonium, an alkanolammonium, and a glucammonium; and (B) an ether carboxylate of Formula (2) $R^2$—O—$(CH_2CH_2O)m$-$CH_2$—COOY (2) wherein —$R^2$ represents a linear or branched $C_{12}$-$C_{22}$ alkyl or alkenyl group, —m represents a number from 0.5 to 20, and —Y represents a hydrogen atom or a cation, selected from the group consisting of an alkali metal, an alkaline earth metal, ammonium, an alkylammonium, an alkanolammonium, and a glucammonium.

$$R^1\text{—O—}(CH_2CH_2O)_n\text{—}CH_2\text{—COOX} \quad (1)$$

$$R^2\text{—O—}(CH_2CH_2O)_m\text{—}CH_2\text{—COOY} \quad (2)$$

10 Claims, No Drawings

CLEANSING COMPOSITION

CROSS REFERENCE TO RELATED APPLICATION

This application is a 371 of PCT/EP2011/067371, filed on Oct. 5, 2011, and claims priority to European Patent Application No. 10 186 522.8, filed on Oct. 5, 2010.

TECHNICAL FIELD

The present invention relates to a cleansing composition.

BACKGROUND ART

Traditionally, personal cleansing was usually carried out using solid soap bars containing alkali metal salts of fatty acids (soaps) as a surfactant. Nowadays, personal cleansing is a daily activity in most countries, and cleansing compositions have to meet customer needs and preferences, such as being very mild, easy applicability, and sufficient lathering. Soap bars are not satisfactory in meeting these requirements, especially in terms of mildness.

Furthermore, in liquid formulations, soap-based systems require adding thickening agents such as highly salt-resistant polymeric components to produce viscosities preferred by consumers. This thickening approach can cause a composition to exhibit dramatic viscoelastic properties during use and impact other product performance attributes (e.g., lathering properties). Because of this, many personal cleansing compositions have been changed to surfactant formulations without soap ingredients. However, many of these formulations fail to provide a preferable rinse feel associated with the cleansed skin. As a result, such a formulation fails to provide a rinse feel similar to that provided by soap, which is desired by many customers, especially those in Asia.

The term "rinse feel" refers to the feeling of the skin when lather is rinsed from the skin following the application of a cleansing composition. The term "soap-like rinse feel" as used herein refers to a feeling similar to that provided by soap; a soap-like rinse feel is a "draggy" rinse feel generated by a friction between the hand and the skin during the rinsing process.

Several attempts have been made to provide cleansing compositions that, while exhibiting mildness, provide the soap-like rinse feel.

For example, Patent Document 1 describes a mild liquid skin cleansing composition with improved lathering and rinse feel, containing: an alkyl ethoxylated sulfate having an average degree of ethoxylation of at least 2.0; an amphoteric surfactant selected from betaine surfactants, imidazoline surfactants, aminoalkanoate surfactants, and iminodialkanoate surfactants; an N-acylamino acid surfactant or a salt thereof; a cationic cellulose ether derivative; 0.2 to 2.0 parts by weight of a $C_8$-$C_{20}$ fatty alcohol; and 0.1 to 5 parts by weight of a water-insoluble salt of a $C_{14}$-$C_{22}$ fatty acid. The viscosity of the composition is within the range of 5000 to 11,000 cps.

Patent Document 2 describes a mild personal cleansing composition containing: (a) 3 to 10 parts by weight of an alkyl ethoxylated sulfate having an average degree of ethoxylation of at least 2.0; (b) 3 to 10 parts by weight of an amphoteric surfactant selected from betaine surfactants, imidazoline surfactants, aminoalkanoate surfactants, and iminodialkanoate surfactants; (c) 0.1 to 3 parts by weight of an N-acylamino acid surfactant or a salt thereof; (d) 0.01 to 0.5 parts by weight of a cationic cellulose ether derivative; (e) 50 to 94 parts by weight of water; and (f) 0.2 to 2.0 parts by weight of a $C_8$-$C_{20}$ fatty alcohol. Also a method of producing a personal cleansing composition is described. It is stated that the composition is mild and lathers well with an improved rinse feel.

Patent Document 3 describes a cleansing composition providing a soap-like rinse feel. The composition contains a lathering surfactant system, specific polymers, and oil ingredients.

Patent Document 4 describes a rinse-off liquid personal cleansing composition containing surfactants and water, wherein the composition contains less than 8% by weight of a first surfactant selected from crystallizing anionic surfactants and contains greater than 3% by weight of a second surfactant selected from non-crystallizing anionic surfactants, amphoteric surfactants, nonionic surfactants, and zwitterionic surfactants.

Patent Document 5 describes a liquid personal cleansing composition containing water, about 1% to about 60% by weight of a water-soluble surfactant, and a water-insoluble oil selected from highly branched poly-α-olefins having a number average molecular weight of about 1000 to about 25,000.

Also, Patent Document 6 describes a liquid personal cleansing composition containing surfactants, water, and water-insoluble oils.

Further, Patent Document 7 describes a liquid personal cleansing composition containing water, surfactants, and 0.5% by weight or greater of water-insoluble oils, wherein the water-insoluble oils provide a mean change in friction meter reading for the composition of 2 or greater as measured by a friction meter technical test method.

As described above, the personal cleansing compositions described in Patent Documents 1 to 7 provide an improved rinse feel. It is stated that these compositions provide an excellent rinse feel, which is a "draggy" and "soap-like" rinse feel, and also are mild to the skin. However, the above compositions cannot be completely considered to provide a soap-like rinse feel, and also they have a different texture from that of soap.

PRIOR ART DOCUMENT

Patent Document

[Patent Document 1] U.S. Pat. No. 5,607,678
[Patent Document 2] WO 96/05798
[Patent Document 3] WO 02/074252
[Patent Document 4] WO 99/09947
[Patent Document 5] WO 99/09949
[Patent Document 6] WO 99/09950
[Patent Document 7] WO 99/09951
EP 2 042 587 relates to a method for lubricating conveyor systems and describes a lubricating composition comprising the following essential elements:
a) one or more phosphoric acid esters of formula (I)

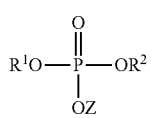

(I)

wherein
$R^1$ represents a linear or branched, saturated or unsaturated $C_6$-$C_{22}$ alkyl and/or alkenyl group, or a $R^3(OCH_2CH_2)_m$ group;

$R^2$ represents hydrogen, a linear or branched, saturated or unsaturated $C_6$-$C_{22}$ alkyl and/or alkenyl group, or $R^3(OCH_2CH_2)_m$ group;

$R^3$ represents hydrogen or a linear or branched, saturated or unsaturated $C_6$-$C_{22}$ alkyl and/or alkenyl group;

m represents a number of from 1 to 15; and

Z represents hydrogen or an appropriate cation;

b) ether carboxylates of formula (II)

$$R\text{—}O\text{—}(OCH_2CH_2O)_n\text{—}CH_2COOM \quad (II)$$

being a mixture of

I) $C_6$-$C_{10}$ alkyl and/or alkenyl ether carboxylates having an average ethoxylation degree from 2 to 8; and II) $C_{12}$-$C_{18}$ alkyl and/or alkenyl ether carboxylates having an average ethoxylation degree from 1 to 10;

wherein M represents hydrogen or an appropriate cation, selected from the group consisting of an alkali metal, an alkaline earth metal, ammonium, an alkylammonium, an alkanolammonium or a glucammonium;

c) one or more $C_6$-$C_{22}$ fatty acids, optionally ethoxylated with 1 to 20 moles of ethylene oxide;

d) one or more $C_6$-$C_{22}$ fatty alcohols, optionally ethoxylated with 1 to 20 moles of ethylene oxide;

e) an inert solvent or mixture thereof, wherein the active matter concentration of the lubricant composition ranges from 1 to 99% by weight.

SUMMARY OF THE INVENTION

Problems to be Solved by the Invention

The present invention relates to a cleansing composition having good foaming properties and having creamy and mild foam qualities while providing an excellent soap-like rinse feel.

Means for Solving the Problems

The present inventors have found that a cleansing composition having good foaming performance and providing creamy and mild foam qualities while providing an excellent rinse feel without leaving a stickiness feel on the skin during drying can be obtained with the use of specific two ether carboxylates in combination.

The present invention provides a cleansing composition containing the following components (A) and (B):

(A) an ether carboxylate of Formula (1)

$$R^1\text{—}O\text{—}(CH_2CH_2O)_n\text{—}CH_2\text{—}COOX \quad (1)$$

wherein $R^1$ represents a linear or branched $C_4$-$C_{10}$ alkyl or alkenyl group, n represents a number from 0.5 to 20, and X represents a hydrogen atom or a cation selected from an alkali metal, an alkaline earth metal, ammonium, an alkylammonium, an alkanolammonium, and a glucammonium; and (B) an ether carboxylate of Formula (2)

$$R^2\text{—}O\text{—}(CH_2CH_2O)_m\text{—}CH_2\text{—}COOY \quad (2)$$

wherein $R^2$ represents a linear or branched $C_{12}$-$C_{22}$ alkyl or alkenyl group, m represents a number from 0.5 to 20, and Y represents a hydrogen atom or a cation selected from an alkali metal, an alkaline earth metal, ammonium, an alkylammonium, an alkanolammonium, and a glucammonium.

Furthermore, the present invention provides a skin cleansing method including applying the cleansing composition to the skin of a body for cleansing, followed by rinsing.

Furthermore, the present invention also relates to the use of a composition comprising the components (A) and (B) for cleansing the skin.

The cleansing composition of the present invention may comprise (C) an anionic surfactant other than (A) and (B), which may be selected from alkyl (ether) sulfates, aryl (ether) sulfates, alkylbenzenesulfonates, alkanesulfonates, olefin sulfonates, alkyl ether sulfonates, glyceryl ether sulfonates, α-methyl ester sulfonates, sulfofatty acid salts, alkyl sulfates, fatty alcohol ether sulfates, glyceryl ether sulfates, hydroxy mixed ether sulfates, monoglyceride (ether) sulfates, fatty acid amide (ether) sulfates, monoalkyl sulfosuccinates, dialkyl sulfosuccinates, monoalkyl sulfosuccinamates, dialkyl sulfosuccinamates, sulfotriglycerides, amide ether carboxylic acids and salts thereof, fatty acid isethionates, fatty acid sarcosinates, and fatty acid taurides; N-acylamino acids such as acyl lactylates, acryl tartrates, acyl glutamates, acyl aspartates; alkyl oligoglucoside sulfates and protein fatty acid condensates (wheat-based vegetable products).

The cleansing composition of the present invention may further comprise (D) an alkanolamide and/or (E) an alkyl hydroxysulfobetaine.

In one embodiment, the composition of the present invention comprises the components (A) and (B) as the only surfactants.

In another embodiment, the composition of the present invention comprises the components (A), (B) and (C), and may optionally also comprise (D), (E) or both, (D) and (E).

In yet another embodiment, the composition of the present invention comprises the components (A), (B) and, in addition, (D), (E) or both, (D) and (E).

Effects of the Invention

The cleansing composition of the present invention has good foam performance such as foaming properties, foam qualities, and the volume of foam, and provides a creamy and mild foam. Further, the cleansing composition provides an excellent rinse feel without leaving a feeling of stickiness on the skin during drying, and therefore provides an excellent feeling upon application.

MODE FOR CARRYING OUT THE INVENTION

Components (A) and (B):

Ether carboxylates are usually obtained by a process including the alkoxylation of an alcohol and subsequent carboxymethylation, as described by Meijer and Smid in Polyether Carboxylates; Anionic Surfactants; Surfactant Science Series, Vol. 56 (pp. 313-361), edited by Helmut W. Stache, ISBN: 0-8247-9394-3.

The alkoxylation of alcohols can be carried out by a common method known by persons skilled in the art. For instance, a polyoxyethylene group is usually obtained by the addition of ethylene oxide to fatty alcohols with an alkaline catalyst such as sodium hydroxide, potassium hydroxide, or sodium methoxide, giving a broad polyoxyethylene oxide distribution (broad degree of ethoxylation). Also, the ethoxylation can be catalyzed by using Lewis acids or by using metallic sodium or sodium hydride to achieve a narrow distribution (narrow degree of ethoxylation). Further, commercially available ethoxylated alcohols can also be used.

Next, the ethoxylated alcohols are reacted with a strong base such as sodium hydroxide or potassium hydroxide in the presence of a reducing agent such as sodium borohydride to obtain the corresponding alkoxylate, which is then carboxymethylated with sodium monochloroacetate (SMCA).

The ether carboxylates of Formula (1) are derived from $C_4$-$C_{10}$ alcohols, preferably from $C_4$-$C_8$ alcohols. Examples of the $C_4$-$C_{10}$ alcohols include n-butanol, n-hexanol, n-octanol, 2-ethylbutanol, 2-methylpentanol, 2-ethylhexanol, 2-methylheptanol, n-decanol, 2-methyl-4-nonanol, 3,7-dimethyl-3-octanol, 3,7-dimethyl-1-octanol, 3,6-dimethyl-3-octanol, or mixtures thereof.

Further, it is preferred that the ether carboxylates of Formula (1) are derived from n-butanol, n-hexanol, 2-methylpentanol, 2-ethylbutanol, n-octanol, 2-ethylhexanol, 2-methylheptanol, or mixtures thereof.

The ether carboxylates of Formula (1) are preferably ones in which $R^1$ is a $C_8$ alkyl group from the viewpoint of feel during rinsing.

The ether carboxylates of Formula (2) are derived from $C_{12}$-$C_{22}$ alcohols, preferably from $C_{12}$-$C_{18}$ alcohols, more preferably from $C_{12}$-$C_{14}$ alcohols.

Examples of the $C_{12}$-$C_{22}$ alcohols suitable for preparing the ether carboxylates of Formula (2) include lauryl alcohol (1-dodecanol), myristyl alcohol (1-tetradecanol), cetyl alcohol (1-hexadecanol), palmitoleyl, alcohol (cis-9-hexadecan-1-ol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z,12Z-octadecadien-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15E-octadecatrien-1-ol), ricinoleyl alcohol (12-hydroxy-9-octadecen-1-ol), arachidyl alcohol (1-eicosanol), behenyl alcohol (1-docosanol), erucyl alcohol (cis-13-docosen-1-ol), and mixtures thereof.

It is preferred that the ether carboxylates of Formula (2) are prepared from lauryl alcohol, myristyl alcohol (1-tetradecanol), cetyl alcohol (1-hexadecanol), or mixtures thereof.

It is preferred that the ether carboxylates of Formula (2) are derived from $C_{12}$-$C_{22}$ alcohols obtained from natural fats and oils. Examples of preferred fats and oils include palm oil, coconut oil, sunflower oil, rapeseed oil, castor oil, olive oil, soybean oil, animal fats and oils such as tallow, fish oil, hardened oils and semihardened oils thereof, and mixtures thereof. As a result of their natural origin, the alcohols that are alkoxylated and carboxymethylated may contain a great variety of alkyl or alkenyl groups, the groups being linear or branched.

It is further preferred that the ether carboxylates of Formula (2) are derived from $C_{12}$-$C_{16}$ alcohols obtainable from coconut oil, palm oil, and olive oil. It is further preferred that the $C_{12}$-$C_{16}$ alcohols to be alkoxylated and carboxymethylated are derived from vegetable oils.

The ether carboxylates of Formula (2) are preferably ones in which $R^2$ is a linear $C_{12}$-$C_{16}$ alkyl group from the viewpoint of foam qualities.

Furthermore, in the $C_{12}$-$C_{22}$ alkyl or alkenyl group in the ether carboxylates of Formula (2), the $C_{12}$-$C_{14}$ proportion is preferably 60% or greater, more preferably 80% or greater, and even more preferably 85% or greater.

According to the present invention, in the ether carboxylates of Formula (1), n is a number preferably from 1 to 12, more preferably from 1 to 9, more preferably from 1 to 8, and even more preferably from 5 to 8. Further, it is preferred that X is a hydrogen atom, sodium, potassium, or magnesium.

According to the present invention, in the ether carboxylates of Formula (2), m is a number preferably from 1 to 12, more preferably from 3 to 10 and even more preferably from 3 to 4.5. Further, it is preferred that Y is a hydrogen atom, sodium, or potassium.

Examples of commercially available ether carboxylates of Formula (1) include AKYPO LF 1 (capryl ether carboxylic acid with an average degree of ethoxylation of 5), AKYPO LF 2 (capryl ether carboxylic acid with an average degree of ethoxylation of 8), AKYPO LF 4 (a mixture of capryl and caproic ether carboxylic acids with an average degree of ethoxylation of 8 and 3, respectively), and AKYPO LF 6 (a mixture of capryl and butyl ether carboxylic acids with an average degree of ethoxylation of 8 and 1, respectively), all marketed by Kao Chemicals Europe.

Among them, AKYPO LF 1 (capryl ether carboxylic acid with an average degree of ethoxylation of 5) and AKYPO LF 2 (capryl ether carboxylic acid with an average degree of ethoxylation of 8) are preferred.

Examples of commercially available ether carboxylic acids or ether carboxylates of Formula (2) include AKYPO RLM 25 (a mixture of lauryl ether carboxylic acid with an average degree of ethoxylation of 3 and myristyl ether carboxylic acid with an average degree of ethoxylation of 3), AKYPO RLM 45CA (a mixture of lauryl ether carboxylic acid with an average degree of ethoxylation of 4.5 and myristyl ether carboxylic acid with an average degree of ethoxylation of 4.5), AKYPO RLM 45NV (a mixture of sodium lauryl ether carboxylate with an average degree of ethoxylation of 4.5 and sodium myristyl ether carboxylate with an average degree of ethoxylation of 4.5), AKYPO RlM 100 (a mixture of lauryl ether carboxylic acid with an average degree of ethoxylation of 10 and myristyl ether carboxylic acid with an average degree of ethoxylation of 10), AKYPO RLM 100NV (a mixture of sodium lauryl ether carboxylate with an average degree of ethoxylation of 10 and sodium myristyl ether carboxylate with an average degree of ethoxylation of 10), AKYPO RO 10 VG (a mixture of oleyl ether carboxylic acid with an average degree of ethoxylation of 1 and cetyl ether carboxylic acid with an average degree of ethoxylation of 1), AKYPO RO 20 VG (a mixture of oleyl ether carboxylic acid with an average degree of ethoxylation of 2 and cetyl ether carboxylic acid with an average degree of ethoxylation of 2), AKYPO RO 50 VG (a mixture of oleyl ether carboxylic acid with an average degree of ethoxylation of 5 and cetyl ether carboxylic acid with an average degree of ethoxylation of 5), and AKYPO RO 90 VG (a mixture of oleyl ether carboxylic acid with an average degree of ethoxylation of 9 and cetyl ether carboxylic acid with an average degree of ethoxylation of 9), all marketed by Kao Chemicals Europe.

Among them, AKYPO RlM 25 (a mixture of lauryl ether carboxylic acid with an average degree of ethoxylation of 3 and myristyl ether carboxylic acid with an average degree of ethoxylation of 3), AKYPO RLM 45CA (a mixture of lauryl ether carboxylic acid with an average degree of ethoxylation of 4.5 and myristyl ether carboxylic acid with an average degree of ethoxylation of 4.5), and AKYPO RLM 45NV (a mixture of sodium lauryl ether carboxylate with an average degree of ethoxylation of 4.5 and sodium myristyl ether carboxylate with an average degree of ethoxylation of 4.5) are preferred.

The cleansing composition of the present invention can contain other anionic, nonionic, and/or amphoteric surfactants together with ether carboxylates of Formulas (1) and (2).

Component (C):

It is preferred that, in addition to an ether carboxylate of Formula (1) and an ether carboxylate of Formula (2), the cleansing composition of the present invention contains one or more anionic surfactants. Addition of anionic surfactants can further improve the foaming properties and the volume of foam.

Examples of preferred anionic surfactants include alkyl (ether) sulfates, aryl (ether) sulfates, alkylbenzenesulfonates, alkanesulfonates, olefin sulfonates, alkyl ether sulfonates, glyceryl ether sulfonates, α-methyl ester sulfonates, sulfofatty acid salts, alkyl sulfates, fatty alcohol ether sulfates, glyceryl ether sulfates, hydroxy mixed ether sulfates, monoglyceride (ether) sulfates, fatty acid amide (ether) sulfates, monoalkyl sulfosuccinates, dialkyl sulfosuccinates, monoalkyl sulfosuccinamates, dialkyl sulfosuccinamates, sulfotriglycerides, amide ether carboxylic acids and salts thereof, fatty acid isethionates, fatty acid sarcosinates, and fatty acid taurides; N-acylamino acids such as acyl lactylates, acryl tartrates, acyl glutamates, acyl aspartates; alkyl oligoglucoside sulfates, protein fatty acid condensates (wheat-based vegetable products), and alkyl (ether) phosphates.

The anionic surfactants of component (C) are preferably alkyl (ether) sulfates of Formula (3)

$$R^3-O-(CH_2CH_2O)_p-SO_3-Z \quad (3)$$

wherein

R$^3$ represents a linear or branched C$_8$-C$_{22}$ alkyl or alkenyl group, p represents a number from 0 to 20, and Z represents a hydrogen atom or a cation selected from an alkali metal, an alkaline earth metal, ammonium, an alkylammonium, an alkanolammonium, and a glucammonium.

Alkyl(ether)sulfates are the salts of sulfuric acid monoesters of (alkoxylated) alcohols. They are prepared by sulfation of alcohols and subsequent neutralization with base, e.g. sodium hydroxide and triethanolamine.

According to the present invention, in Formula (3), R$^3$ is preferably a linear or branched C$_2$-C$_{18}$ alkyl or alkenyl group, more preferably a linear or branched C$_{12}$-C$_{14}$ alkyl or alkenyl group.

In Formula (3), p is a number preferably from 0.5 to 12, more preferably from 0.5 to 5, even more preferably from 0.5 to 3.

Examples of commercially available alkyl(ether)sulfates of Formula (3) include EMAL 10, EMAL 10N, EMAL 10P-HD, EMAL 10G, EMAL 30E, EMAL 270E, EMAL 270D, EMAL 227E, EMAL 22813, and EMAL 40TE, all marketed by Kao Chemicals Europe.

(D) Nonionic Surfactants:

The cleansing composition of the present invention can further contain a nonionic surfactant. Addition of a nonionic surfactant can improve the volume of foam.

Examples of preferred nonionic surfactants include alkanolamides, alkoxylated alkanolamides, alkoxylated trimethylolpropanes, alkoxylated 1,2,3-trihydroxy hexanes, alkoxylated pentaerythritols, alkoxylated sorbitols, alkoxylated glycerin fatty acid esters, alkoxylated trimethylolpropane fatty acid esters, alkoxylated 1,2,3-trihydroxy hexane fatty acid esters, alkoxylated pentaerythritol fatty acid esters, alkoxylated sorbitol fatty acid esters, fatty alcohol polyglycol ethers, alkylphenol polyglycol ethers, fatty acid polyglycol esters, fatty acid amide polyglycol ethers, fatty amine polyglycol ethers, partly oxidized alkyl or alkenyl oligoglycosides or glucuronic acid derivatives, fatty acid-N-alkylglucamides, protein hydrolysates (wheat-based vegetable products), polyol fatty acid esters, sugar esters, alkyl polyglucosides, sorbitan esters, and polysorbates.

Examples of commercially available nonionic surfactants include AMIDET N, AMIDET A15, AMIDET A/17, AMIDET A/26, AMIDET A-111-P, AMIDET B-112, LEVENOL H&B, LEVENOL C-301, LEVENOL C-201, and MYDOL-10, all marketed by Kao Chemicals Europe and Kao Corporation.

It is preferred that the cleansing composition of the present invention contains an alkanolamide-type nonionic surfactant. Examples of the alkanolamide-type nonionic surfactants include Cocamide MEA, Cocamide DEA, PEG-4 Rapeseedamide, Trideceth-2 Carboxamide MEA, PEG-5 Cocamide, PEG-6 Cocamide, and PEG-14 Cocamide.

(E) Amphoteric Surfactants

The cleansing composition of the present invention can further contain an amphoteric surfactant in order to improve performance such as viscosity, hard water tolerance, stability, and foaming properties. Amphoteric surfactants include ampholytes and betaines. Examples of the amphoteric surfactants include alkyl betaines, alkyl sulfobetaines (sultaines), amidoalkyl betaines, alkyl glycinates, alkyl carboxyglycinates, alkyl amphopropionates, alkyl amphoglycinates, alkyl amidopropyl betaines, and hydroxysultaines.

Examples of preferred amphoteric surfactants include alkyl amidopropyl betaines, alkyl amidopropyl hydroxysultaines, alkyl hydroxysultaines, and alkyl amphoacetates.

Examples of commercially available amphoteric surfactants include BETADET HR, BETADET HR-50K, BETADET S-20, BETADET SHR, and BETADET THC-2, all marketed by Kao Chemicals Europe.

Cleansing Compositions:

The cleansing composition of the present invention contains (A) an ether carboxylate of Formula (1) and (B) an ether carboxylate of Formula (2) and provides a soap-like rinse feel. Further, a cleansing composition having foamability, especially good foaming properties and creamy foam qualities, while leaving no stickiness feel on the skin during drying can be obtained with a combination of components (A) and (B).

The weight ratio of component (A) to component (B), (A):(B), is preferably 5:1 to 1:5, more preferably 3:1 to 1:3, and even more preferably 2:1 to 1:2.

A combination of (A) an ether carboxylate of Formula (1) wherein R$^1$ is a linear C$_8$ alkyl group, an average degree of ethoxylation of n is 5 to 8, and X is an alkali metal, and (B) an ether carboxylate of Formula (2) wherein R$^2$ is a linear C$_{12}$-C$_{16}$ alkyl group, an average degree of ethoxylation of m is 3 to 4.5, and Y is an alkali metal is most preferable from the viewpoint of attaining both a soap-like rinse feel and good foamability.

It is preferred that the cleansing composition of the present invention contains (A) an ether carboxylate of Formula (1), (B) an ether carboxylate of Formula (2), and further (C) an anionic co-surfactant.

Also, it is preferred that the cleansing composition of the present invention contains (A) an ether carboxylate of Formula (1), (B) an ether carboxylate of Formula (2), and (C) an alkyl(ether)sulfate of Formula (3).

The weight ratio of component (A) to component (C), (A):(C), is preferably 10:1 to 1:2, more preferably 8:1 to 1:1, and even more preferably 6:1 to 1:1.

It is preferred that the cleansing composition of the present invention contains:

(A) an ether carboxylate of Formula (1);
(B) an ether carboxylate of Formula (2);
(C) an anionic co-surfactant, preferably an alkyl(ether)sulfate of Formula (3);
(D) a nonionic surfactant, and/or (E) an amphoteric surfactant.

The weight ratio of component (A) to component (D), (A):(D), is preferably 8:1 to 1:3, more preferably 6:1 to 1:1, and even more preferably 3:1 to 1:1.

Further, it is preferred that the cleansing composition of the present invention contains:
(A) an ether carboxylate of Formula (1);
(B) an ether carboxylate of Formula (2);
(C) an alkyl(ether)sulfate of Formula (3);
(D) an alkanolamide; and
(E) an alkyl hydroxysultaine.

Each component may be used alone or in combination of two or more in the present invention.

The content of component (A) is preferably 0.1 to 30% by weight, more preferably 0.5 to 20% by weight, even more preferably 2 to 15% by weight, and even more preferably 2 to 8% by weight in the total composition.

The content of component (B) is preferably 0.1 to 20% by weight, more preferably 0.5 to 15% by weight, even more preferably 2 to 12% by weight, and even more preferably 2 to 8% by weight in the total composition.

The content of component (C) is preferably 0 to 15% by weight, more preferably 0.5 to 10% by weight, even more preferably 0.75 to 10% by weight, and even more preferably 1.5 to 4% by weight in the total composition.

The content of component (D) is preferably 0 to 5% by weight, more preferably 0.5 to 4% by weight, and even more preferably 1.0 to 3% by weight in the total composition.

The content of component (E) is preferably 0 to 5% by weight, more preferably 0.5 to 5% by weight, and even more preferably 0.5 to 4% by weight in the total composition.

It is preferred that the cleansing composition of the present invention contains, as the surfactants:
(A) 0.1 to 30% by weight of an ether carboxylate of Formula (1);
(B) 0.1 to 30% by weight of an ether carboxylate of Formula (2); and
(C) 0 to 15% by weight of an alkyl(ether)sulfate of Formula (3).

Further, it is preferred that the cleansing composition of the present invention contains, as the surfactants:
(A) 0.5 to 20% by weight of an ether carboxylate of Formula (1);
(B) 0.5 to 15% by weight of an ether carboxylate of Formula (2); and
(C) 0 to 10% by weight of an alkyl(ether)sulfate of Formula (3).

Further, it is preferred that the cleansing composition of the present invention contains, as the surfactants:
(A) 2 to 15% by weight of an ether carboxylate of Formula (1);
(B) 2 to 12% by weight of an ether carboxylate of Formula (2); and
(C) 1 to 8% by weight of an alkyl(ether)sulfate of Formula (3).

It is preferred that the cleansing composition of the present invention contains, as the surfactants:
(A) 2 to 15% by weight of an ether carboxylate of Formula (1);
(B) 2 to 12% by weight of an ether carboxylate of Formula (2);
(C) 0.5 to 10% by weight of an alkyl(ether)sulfate of Formula (3);
(D) 0.5 to 5% by weight of a nonionic surfactant; and
(E) 0.5 to 5% by weight of an amphoteric surfactant.

Further, it is preferred that the cleansing composition of the present invention contains, as the surfactants:
(A) 2 to 8% by weight of an ether carboxylate of Formula (1);
(B) 2 to 8% by weight of an ether carboxylate of Formula (2);
(C) 0.5 to 4% by weight of an alkyl(ether)sulfate of Formula (3);
(D) 0.5 to 4% by weight of an alkanolamide; and
(E) 0.5 to 4% by weight of an alkyl hydroxysultaine.

The total content of the surfactants in the cleansing composition of the present invention is preferably 0.5 to 30% by weight, more preferably 5 to 25% by weight, and even more preferably 10 to 20% by weight in the total composition. The surfactants are any of components (A) and (B); components (A), (B), and (C); components (A), (B), (C), and (D); and components (A), (B), (C), (D), and (E), as mentioned above.

The cleansing composition of the present invention contains (F) water, which constitutes the balance of the composition after mixing each component. It is preferred that component (F) is contained in an amount of 10 to 94.5% by weight, more preferably 15 to 90% by weight, in the total composition.

In addition, components used in a conventional cleansing composition such as solvents, coloring agents, inorganic salts, organic salts, viscosity adjusting agents, fragrances, fungicides, antiphlogistics, chelating agents, foaming promoting agents, antiseptics, and moisturizing agents may be incorporated into the cleansing composition of the present invention, to the extent that the effect of the invention is not impaired.

The cleansing composition of the present invention is produced by mixing components by a conventional method, and it is preferably prepared as a liquid aqueous preparation.

The pH is preferably 3 to 12, more preferably 5 to 10.5. It is to be noted that the pH is a value obtained by measuring a 20-fold dilution of each cleansing composition in ion-exchange water.

The cleansing composition of the present invention may be provided as, for example, a facial wash, a body soap, a hand soap, and a hair shampoo. The cleansing composition of the present invention is suitable as a skin cleansing agent such as a facial wash and a body soap.

The cleansing composition of the present invention is suitable for cleansing the skin by applying an effective amount of the composition.

Examples of a method for cleansing the skin with the cleansing composition of the present invention include the following. That is, a method in which an adequate amount of the cleansing composition of the present invention is applied to the body, namely the skin of the body such as the face, hands, feet, and torso, and after lathering up and washing the body, the composition is rinsed off with warm water, for example from a shower. Further, the body can be lathered up and washed with the cleansing composition using a cleansing aid such as a towel, a sponge, or a brush.

Further, the present invention relates to the use of a composition containing (A) an ether carboxylate of Formula (1) and (B) an ether carboxylate of Formula (2) in a cleansing system, preferably in a cleansing system for the skin.

Hereinbelow, the present invention will be described with Examples; however, the present invention is not limited to these Examples.

EXAMPLES

Examples 1 to 43, Comparative Examples 1 to 14

Cleansing compositions were produced according to the compositions shown in Tables 1 to 9 and evaluated for their foaming properties, foam qualities, volume of foam, rinse feel, and non-stickiness during drying. The results are also shown in Tables 1 to 9.

(Production Method)

Each component shown in Tables 1 to 9 (except sodium hydroxide) and water were mixed, and the resulting mixture was heated to 70° C. and homogenized. Subsequently, sodium hydroxide was added in such an amount that the pH was 6, and the resulting mixture was stirred and homogenized. Further, the mixture was cooled to room temperature while stirring, whereby each cleansing composition was obtained.

(Evaluation Method)

An expert panel of three panelists conducted the following hand wash evaluation test using each cleansing composition, and organoleptically evaluated foaming properties, foam qualities, the volume of foam, rinse feel, and non-stickiness during drying, and judged each cleansing composition according to the following judgment criteria.

(Hand Wash Evaluation Test)

Both hands were wetted with water (approximately 5 g) and 1 g of the cleansing composition was placed on the palm of one hand. Water (approximately 5 g) was further added onto the composition, followed by lathering by rubbing the palms of both hands together. After lathering for 15 seconds, foaming properties, foam qualities, and the volume of foam were evaluated.

Subsequently, the composition was rinsed off with running water for about 15 seconds, and then the rinse feel was evaluated.

After rinsing off, water droplets on both hands were wiped off with dry cotton towels, and non-stickiness during drying was evaluated while rubbing the palms of both hands.

(Judgment Criteria)

An expert panel of three panelists gives scores for each evaluation item from five points (good) to one point (poor) in increments of 0.5, by setting AKYPO LF 2 (Comparative Example 3) at one point as the reference. Subsequently, the average of the scores given by the three expert panelists were calculated for each item, and the average score was used as an index for evaluation of each item.

TABLE 1

| | Components (% by weight) | Examples | | | | | | | Comparative Examples | |
|---|---|---|---|---|---|---|---|---|---|---|
| | | 1 | 2 | 3 | 4 | 5 | 6 | 7 | 1 | 2 |
| A | Polyoxyethylene (5) capryl ether carboxylic acid*2 | 12.5 | 11.3 | 10.0 | 7.5 | 5.0 | 3.8 | 2.5 | 15.0 | 0.0 |
| B | Mixture of sodium polyoxyethylene (4.5) lauryl ether carboxylate and sodium polyoxyethylene (4.5) myristyl ether carboxylate*3 | 2.5 | 3.8 | 5.0 | 7.5 | 10.0 | 11.3 | 12.5 | 0.0 | 15.0 |
| F | Water | Balance | Balance | Balance | Balance | Balance | Balance | Balance | Balance | Balance |
| | Sodium hydroxide | q.s.*1 | q.s.*1 | q.s.*1 | q.s.*1 | q.s.*1 | q.s.*1 | q.s.*1 | q.s.*1 | q.s.*1 |
| | Total | 100 | 100 | 100 | 100 | 100 | 100 | 100 | 100 | 100 |
| | A:B | 5:1 | 3:1 | 2:1 | 1:1 | 1:2 | 1:3 | 1:5 | — | — |
| | Foaming properties | 1.2 | 1.2 | 1.5 | 1.7 | 2.0 | 1.5 | 1.5 | 1.0 | 1.0 |
| | Foam quality | 1.2 | 1.2 | 1.5 | 1.7 | 1.7 | 1.5 | 1.5 | 1.0 | 1.0 |
| | Volume of foam | 1.2 | 1.2 | 2.0 | 2.0 | 2.0 | 2.0 | 1.5 | 1.0 | 1.0 |
| | Rinse feel | 2.0 | 2.0 | 2.0 | 2.0 | 2.0 | 2.0 | 1.5 | 1.5 | 1.0 |
| | Non-stickiness during drying | 2.5 | 3.0 | 3.0 | 3.5 | 3.5 | 3.5 | 3.5 | 1.0 | 3.5 |

*1The pH of the system was adjusted to 6 with addition of an adequate amount of sodium hydroxide.
*2AKYPO LF 1(manufactured by Kao Chemicals Europe)
*3AKYPO RLM 45NV (manufactured by Kao Chemicals Europe)

TABLE 2

| | Components (% by weight) | Examples | | | | | | | Comparative Examples | |
|---|---|---|---|---|---|---|---|---|---|---|
| | | 8 | 9 | 10 | 11 | 12 | 13 | 14 | 3 | 2 |
| A | Polyoxyethylene (8) capryl ether carboxylic acid*4 | 12.5 | 11.3 | 10.0 | 7.5 | 5.0 | 3.8 | 2.5 | 15.0 | 0.0 |
| B | Mixture of sodium polyoxyethylene (4.5) lauryl ether carboxylate and sodium polyoxyethylene (4.5) myristyl ether carboxylate *3 | 2.5 | 3.8 | 5.0 | 7.5 | 10.0 | 11.3 | 12.5 | 0.0 | 15.0 |
| F | Water | Balance | Balance | Balance | Balance | Balance | Balance | Balance | Balance | Balance |
| | Sodium hydroxide | q.s.*1 | q.s.*1 | q.s.*1 | q.s.*1 | q.s.*1 | q.s.*1 | q.s.*1 | q.s.*1 | q.s.*1 |
| | Total | 100 | 100 | 100 | 100 | 100 | 100 | 100 | 100 | 100 |
| | A:B | 5:1 | 3:1 | 2:1 | 1:1 | 1:2 | 1:3 | 1:5 | — | — |
| | Foaming properties | 1.5 | 1.5 | 2.0 | 2.0 | 2.0 | 1.5 | 1.5 | 1.0 | 1.0 |
| | Foam quality | 1.5 | 1.5 | 1.7 | 1.7 | 1.7 | 1.7 | 1.5 | 1.0 | 1.0 |
| | Volume of foam | 1.5 | 1.5 | 2.0 | 2.0 | 2.0 | 1.5 | 1.5 | 1.0 | 1.0 |
| | Rinse feel | 2.0 | 2.0 | 2.0 | 2.0 | 2.0 | 1.5 | 1.5 | 1.0 | 1.0 |
| | Non-stickiness during drying | 2.5 | 3.0 | 3.0 | 3.5 | 3.5 | 3.5 | 3.5 | 1.0 | 3.5 |

*4AKYPO LF 2 (manufactured by Kao Chemicals Europe)

TABLE 3

| | Components (% by weight) | Examples | | | | | | | Comparative Examples | |
|---|---|---|---|---|---|---|---|---|---|---|
| | | 15 | 16 | 17 | 18 | 19 | 20 | 21 | 1 | 4 |
| A | Polyoxyethylene (5) capryl ether carboxylic acid*2 | 12.5 | 11.3 | 10.0 | 7.5 | 5.0 | 3.8 | 2.5 | 15.0 | 0.0 |
| B | Mixture of sodium polyoxyethylene (10) lauryl ether carboxylate and sodium polyoxyethylene (10) myristyl ether carboxylate*5 | 2.5 | 3.8 | 5.0 | 7.5 | 10.0 | 11.3 | 12.5 | 0.0 | 15.0 |
| F | Water | Balance | Balance | Balance | Balance | Balance | Balance | Balance | Balance | Balance |
| | Sodium hydroxide | q.s.*1 | q.s.*1 | q.s.*1 | q.s.*1 | q.s.*1 | q.s.*1 | q.s.*1 | q.s.*1 | q.s.*1 |
| | Total | 100 | 100 | 100 | 100 | 100 | 100 | 100 | 100 | 100 |
| | A:B | 5:1 | 3:1 | 2:1 | 1:1 | 1:2 | 1:3 | 1:5 | — | — |
| | Foaming properties | 1.0 | 1.2 | 1.2 | 1.2 | 1.5 | 1.5 | 1.5 | 1.0 | 1.0 |
| | Foam quality | 1.0 | 1.2 | 1.2 | 1.2 | 1.5 | 1.0 | 1.0 | 1.0 | 1.0 |
| | Volume of foam | 1.0 | 1.2 | 1.2 | 1.2 | 1.5 | 1.5 | 1.5 | 1.0 | 1.0 |
| | Rinse feel | 2.0 | 2.0 | 2.0 | 2.0 | 2.0 | 2.0 | 2.0 | 1.5 | 1.0 |
| | Non-stickiness during drying | 3.0 | 3.0 | 3.0 | 3.0 | 3.0 | 3.0 | 3.0 | 1.0 | 3.0 |

*5AKYPO RLM 100NV (manufactured by Kao Chemicals Europe)

TABLE 4

| | Components (% by weight) | Examples | | | | | | | Comparative Examples | |
|---|---|---|---|---|---|---|---|---|---|---|
| | | 22 | 23 | 24 | 25 | 26 | 27 | 28 | 3 | 4 |
| A | Polyoxyethylene (8) capryl ether carboxylic acid*4 | 12.5 | 11.3 | 10.0 | 7.5 | 5.0 | 3.8 | 2.5 | 15.0 | 0.0 |
| B | Mixture of sodium polyoxyethylene (10) lauryl ether carboxylate and sodium polyoxyethylene (10) myristyl ether carboxylate *5 | 2.5 | 3.8 | 5.0 | 7.5 | 10.0 | 11.3 | 12.5 | 0.0 | 15.0 |
| F | Water | Balance | Balance | Balance | Balance | Balance | Balance | Balance | Balance | Balance |
| | Sodium hydroxide | q.s.*1 | q.s.*1 | q.s.*1 | q.s.*1 | q.s.*1 | q.s.*1 | q.s.*1 | q.s.*1 | q.s.*1 |
| | Total | 100 | 100 | 100 | 100 | 100 | 100 | 100 | 100 | 100 |
| | A:B | 5:1 | 3:1 | 2:1 | 1:1 | 1:2 | 1:3 | 1:5 | — | — |
| | Foaming properties | 1.2 | 1.2 | 1.2 | 1.2 | 1.5 | 1.5 | 1.0 | 1.0 | 1.0 |
| | Foam quality | 1.2 | 1.2 | 1.2 | 1.2 | 1.5 | 1.5 | 1.5 | 1.0 | 1.0 |
| | Volume of foam | 1.2 | 1.2 | 1.2 | 1.2 | 1.5 | 1.5 | 1.0 | 1.0 | 1.0 |
| | Rinse feel | 2.0 | 2.0 | 2.0 | 2.0 | 2.0 | 2.0 | 1.5 | 1.0 | 1.0 |
| | Non-stickiness during drying | 3.0 | 3.0 | 3.0 | 3.0 | 3.0 | 3.0 | 3.0 | 1.0 | 3.0 |

TABLE 5

|   | Components (% by weight) | Examples 29 | Comparative Examples 3 | Comparative Examples 6 |
|---|---|---|---|---|
| A | Polyoxyethylene (8) capryl ether carboxylic acid*4 | 7.5 | 15.0 | 0.0 |
| B | Mixture of polyoxyethylene (3) lauryl ether carboxylic acid and polyoxyethylene (3) myristyl ether carboxylic acid*6 | 7.5 | 0.0 | 15.0 |
| F | Water | Balance | Balance | Balance |
|   | Sodium hydroxide | q.s.*1 | q.s.*1 | q.s.*1 |
|   | Total | 100 | 100 | 100 |
|   | A:B | 1:1 | — | — |
|   | Foaming properties | 2.2 | 1.0 | 1.5 |
|   | Foam quality | 2.2 | 1.0 | 1.0 |
|   | Volume of foam | 2.2 | 1.0 | 1.0 |
|   | Rinse feel | 2.5 | 1.0 | 1.5 |
|   | Non-stickiness during drying | 4.0 | 1.0 | 4.0 |

*6AKYPO RLM 25 (manufactured by Kao Chemicals Europe)

TABLE 6

|   | Components (% by weight) | Examples 30 | Examples 31 | Comparative Examples 7 | Comparative Examples 8 | Comparative Examples 9 | Comparative Examples 10 | Comparative Examples 11 |
|---|---|---|---|---|---|---|---|---|
| A | Polyoxyethylene (8) capryl ether carboxylic acid*4 | 5.0 | 3.3 | 0.0 | 0.0 | 0.0 | 0.0 | 0.0 |
| B | Mixture of polyoxyethylene (3) lauryl ether carboxylic acid and polyoxyethylene (3) myristyl ether carboxylic acid *6 | 5.0 | 3.3 | 5.0 | 0.0 | 0.0 | 0.0 | 0.0 |
| C | Sodium polyoxyethylene (2) lauryl ether sulfate | 0.0 | 3.3 | 5.0 | 10.0 | 16.0 | 0.0 | 0.0 |
| D | Polyoxyethylene (4) rapeseed fatty acid amide | 3.0 | 3.0 | 3.0 | 3.0 | 0.0 | 16.0 | 0.0 |
| E | Lauryl hydroxysultaine | 3.0 | 3.0 | 3.0 | 3.0 | 0.0 | 0.0 | 16.0 |
| F | Water | Balance | Balance | Balance | Balance | Balance | Balance | Balance |
|   | Sodium hydroxide | q.s.*1 | q.s.*1 | q.s.*1 | q.s.*1 | q.s.*1 | q.s.*1 | q.s.*1 |
|   | Total | 100 | 100 | 100 | 100 | 100 | 100 | 100 |
|   | A:B | 1:1 | 1:1 | — | — | — | — | — |
|   | A:C | — | 1:1 | — | — | — | — | — |
|   | A:D | 5:3 | 1:0.9 | — | — | — | — | — |
|   | Foaming properties | 3.3 | 3.0 | 2.3 | 2.2 | 2.0 | 1.0 | 1.0 |
|   | Foam quality | 3.3 | 3.8 | 2.0 | 1.5 | 1.5 | 1.0 | 1.0 |
|   | Volume of foam | 3.3 | 3.0 | 2.0 | 2.2 | 2.0 | 1.0 | 1.0 |
|   | Rinse feel | 2.5 | 2.5 | 1.0 | 1.0 | 1.0 | 1.0 | 1.0 |
|   | Non-stickiness during drying | 4.0 | 4.0 | 2.0 | 1.5 | 1.0 | 1.0 | 1.0 |

TABLE 7

|   | Components (% by weight) | Examples 32 | Examples 33 | Examples 34 | Examples 35 | Examples 36 | Examples 37 |
|---|---|---|---|---|---|---|---|
| A | Polyoxyethylene (8) capryl ether carboxylic acid*4 | 0.1 | 0.5 | 2.0 | 8.0 | 15.0 | 7.5 |
| B | Mixture of polyoxyethylene (3) lauryl ether carboxylic acid and polyoxyethylene (3) myristyl ether carboxylic acid *6 | 0.1 | 0.5 | 2.0 | 8.0 | 7.5 | 15.0 |
| C | Sodium polyoxyethylene (2) lauryl ether sulfate | 15.0 | 3.3 | 4.0 | 0.75 | 1.5 | 0.94 |
| D | Polyoxyethylene (4) rapeseed fatty acid amide | 4.0 | 3.0 | 2.0 | 2.6 | 0.5 | 1.25 |
| E | Lauryl hydroxysultaine | 3.0 | 4.0 | 3.0 | 3.0 | 1.0 | 0.5 |
| F | Water | Balance | Balance | Balance | Balance | Balance | Balance |
|   | Sodium hydroxide | q.s.*1 | q.s.*1 | q.s.*1 | q.s.*1 | q.s.*1 | q.s.*1 |
|   | Total | 100 | 100 | 100 | 100 | 100 | 100 |
|   | A:B | 1:1 | 1:1 | 1:1 | 1:1 | 2:1 | 1:2 |
|   | A:C | 1:150 | 1:6.6 | 1:2 | 11:1 | 10:1 | 8:1 |
|   | A:D | 1:40 | 1:6 | 1:1 | 3:1 | 30:1 | 6:1 |
|   | Foaming properties | 2.7 | 2.0 | 2.8 | 3.0 | 3.0 | 2.8 |
|   | Foam quality | 1.5 | 2.7 | 3.8 | 4.0 | 4.0 | 3.5 |

TABLE 7-continued

|   | | | Examples | | | |
| Components (% by weight) | 32 | 33 | 34 | 35 | 36 | 37 |
| --- | --- | --- | --- | --- | --- | --- |
| Volume of foam | 2.5 | 2.0 | 3.0 | 3.0 | 2.5 | 2.8 |
| Rinse feel | 1.3 | 2.0 | 2.5 | 2.5 | 3.0 | 2.5 |
| Non-stickiness during drying | 1.7 | 2.0 | 4.0 | 4.0 | 3.0 | 4.0 |

TABLE 8

| | Components (% by weight) | 38 | 39 | 40 | 41 |
| --- | --- | --- | --- | --- | --- |
| A | Polyoxyethylene (8) capryl ether carboxylic acid*4 | 6.0 | 4.0 | 5.0 | 4.0 |
| B | Mixture of polyoxyethylene (3) lauryl ether carboxylic acid and polyoxyethylene (3) myristyl ether carboxylic acid*6 | 3.0 | 4.0 | 2.5 | 4.0 |
| C | Sodium polyoxyethylene (2) lauryl ether sulfate | 1.0 | 8.0 | 0.5 | 4.0 |
| F | Water | Balance | Balance | Balance | Balance |
| | Sodium hydroxide | q.s.*1 | q.s.*1 | q.s.*1 | q.s.*1 |
| | Total | 100 | 100 | 100 | 100 |
| | A:B | 2:1 | 1:1 | 2:1 | 1:1 |
| | A:C | 6:1 | 1:2 | 10:1 | 1:1 |
| | Foaming properties | 1.8 | 2.3 | 1.7 | 2.3 |
| | Foam quality | 2.0 | 2.3 | 1.7 | 2.3 |
| | Volume of foam | 2.0 | 3.0 | 2.0 | 2.7 |
| | Rinse feel | 3.0 | 2.0 | 2.7 | 2.5 |
| | Non-stickiness during drying | 3.0 | 3.0 | 3.0 | 3.5 |

TABLE 9

| | | Examples | | Comparative Examples | | |
| --- | --- | --- | --- | --- | --- | --- |
| | Components (% by weight) | 42 | 43 | 12 | 13 | 14 |
| A | Mixture of polyoxyethylene (8) capryl ether carboxylic acid andpolyoxyethylene (3) hexyl ether carboxylic acid *7 | 7.5 | | 15 | | |
| | Mixture of polyoxyethylene (8) capryl ether carboxylic acid andpolyoxyethylene (1) butyl ether carboxylic acid *8 | | 7.5 | | 15 | |
| B | Mixture of polyoxyethylene (5) oleyl ether carboxylic acid andpolyoxyethylene (5) cetyl ether carboxylic acid *9 | 7.5 | 7.5 | | | 15 |
| F | Water | Balance | Balance | Balance | Balance | Balance |
| | Sodium hydroxide | q.s.*1 | q.s.*1 | q.s.*1 | q.s.*1 | q.s.*1 |
| | Total | 100 | 100 | 100 | 100 | 100 |
| | A:B | 1:1 | 1:1 | — | — | — |
| | Foaming properties | 1.5 | 1.5 | 1 | 1 | 1.2 |
| | Foam quality | 1.5 | 1.5 | 1 | 1 | 1 |
| | Volume of foam | 1.5 | 1.5 | 1 | 1 | 1 |
| | Rinse feel | 1.5 | 1.5 | 1 | 1 | 1 |
| | Non-stickiness during drying | 3 | 3 | 1 | 1 | 3 |

*7: AKYPO LF 4 (manufactured by Kao Chemicals Europe)
*8: AKYPO LF 6 (manufactured by Kao Chemicals Europe)
*9: AKYPO RO 50(VG) (manufactured by Kao Chemicals Europe)

What is claimed is:

1. A skin cleansing method comprising:
applying, to the skin of a body for washing, a cleansing composition,
followed by rinsing the cleansing composition from the skin,
wherein the cleaning composition comprises:
(A) 0.5 to 8% by weight of at least one ether carboxylate of Formula (1);
(B) 0.5 to 8% by weight of at least one ether carboxylate of Formula (2);
(C) 0.5 to 4% by weight of at least one alkyl (ether) sulfate of Formula (3);
(D) 0.5 to 4% by weight of at least one alkanolamide; and
(E) 0.5 to 4% by weight of at least one alkyl hydroxysulfobetaine,
Formula (1) is:

$R^1$ is a linear or branched $C_4$-$C_{10}$ alkyl or alkenyl group,
n is a number from 0.5 to 20, X is a hydrogen atom or a cation selected from the group consisting of an alkali metal, an alkaline earth metal, ammonium, an alkylammonium, an alkanolammonium, and a glucammonium, Formula (2) is:

$R^2$ is a linear or branched $C_{12}$-$C_{16}$ alkyl or alkenyl group, m is a number from 0.5 to 20, Y is a hydrogen atom or a cation selected from the group consisting of an alkali metal, an alkaline earth metal, ammonium, an alkylammonium, an alkanolammonium, and a glucammonium, Formula (3) is:

$R^3$ is a linear or branched $C_8$-$C_{22}$ alkyl or alkenyl group, p is a number from 0 to 20, and Z is a hydrogen atom or a cation selected from the group consisting of an alkali metal, an alkaline earth metal, ammonium, an alkylammonium, an alkanolammonium, and a glucammonium.

2. The skin cleansing method according to claim 1, wherein $R^1$ in Formula (1) is a $C_4$-$C_8$ alkyl or alkenyl group.

3. The skin cleansing method according to claim 1, wherein n in Formula (1) is a number from 1 to 9.

4. The skin cleansing method according to claim 1, wherein X in Formula (1) is a hydrogen atom, sodium, or potassium.

5. The skin cleansing method according to claim 1, wherein m in Formula (2) is a number from 1 to 12.

6. The skin cleansing method according to claim 1, wherein Y in Formula (2) is a hydrogen atom, sodium, or potassium.

7. The skin cleansing method according to claim 1, wherein, in said cleansing composition, a weight ratio of component (A) to component (B), (A):(B), is 5:1 to 1:5.

8. The skin cleansing method according to claim 1, wherein, in said cleansing composition, a weight ratio of component (A) to component (C), (A):(C), is 10:1 to 1:2.

9. The skin cleansing method according to claim 1, wherein, in said cleansing composition, a weight ratio of component (A) to component (D), (A):(D), is 6:1 to 1:1.

10. The skin cleansing method according to claim 1, wherein a total content of the surfactants is 5 to 25% by weight in the total composition.

* * * * *

UNITED STATES PATENT AND TRADEMARK OFFICE
CERTIFICATE OF CORRECTION

PATENT NO. : 9,271,909 B2
APPLICATION NO. : 13/877969
DATED : March 1, 2016
INVENTOR(S) : Pilar Castan Barberan et al.

It is certified that error appears in the above-identified patent and that said Letters Patent is hereby corrected as shown below:

Claims

Column 17, line 63, claim 1, "whereinthe cleaning composition comprises:" should read --wherein the cleansing composition comprises:--

Signed and Sealed this
Twelfth Day of July, 2016

Michelle K. Lee
*Director of the United States Patent and Trademark Office*